(12) United States Patent
Aferzon et al.

(10) Patent No.: US 8,029,569 B2
(45) Date of Patent: Oct. 4, 2011

(54) IMPLANTABLE SPINAL DISK

(75) Inventors: Joseph Aferzon, Avon, CT (US); Jeffrey A. Bash, West Hartford, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 940 days.

(21) Appl. No.: 11/939,991

(22) Filed: Nov. 14, 2007

(65) Prior Publication Data
US 2008/0183295 A1 Jul. 31, 2008

Related U.S. Application Data

(60) Provisional application No. 60/859,990, filed on Nov. 20, 2006.

(51) Int. Cl.
*A61F 2/44* (2006.01)
(52) U.S. Cl. .................... 623/17.15; 623/17.12
(58) Field of Classification Search ..... 623/17.11–17.16
See application file for complete search history.

(56) References Cited

U.S. PATENT DOCUMENTS

| | | | | |
|---|---|---|---|---|
| 4,874,389 A | * | 10/1989 | Downey | 623/17.16 |
| 4,946,378 A | * | 8/1990 | Hirayama et al. | 623/17.16 |
| 6,136,031 A | * | 10/2000 | Middleton | 623/17.16 |
| 6,350,283 B1 | | 2/2002 | Michelson | |
| 6,602,291 B1 | | 8/2003 | Ray et al. | |
| 6,656,224 B2 | * | 12/2003 | Middleton | 623/17.16 |
| 6,758,861 B2 | * | 7/2004 | Ralph et al. | 623/17.13 |
| 6,770,094 B2 | * | 8/2004 | Fehling et al. | 623/17.13 |
| 6,958,077 B2 | | 10/2005 | Suddaby | |
| 6,969,405 B2 | | 11/2005 | Suddaby | |
| 6,981,989 B1 | | 1/2006 | Fleischmann et al. | |
| 7,060,100 B2 | * | 6/2006 | Ferree et al. | 623/17.16 |
| 7,128,762 B2 | * | 10/2006 | Middleton | 623/17.16 |
| 7,166,131 B2 | | 1/2007 | Studer et al. | |

(Continued)

FOREIGN PATENT DOCUMENTS
EP 1103237 A2 5/2001
(Continued)

OTHER PUBLICATIONS

Charite Artificial Disc, "The Worlds First Artificial Disc", [Online]. [retrieved Aug. 10, 2007]. Retrieved from the internet: ,URL: Http://Charitedisc.com/charitedev/domestic/patients/about_worldfirst.asp>,2 pgs.

(Continued)

*Primary Examiner* — Eduardo C Robert
*Assistant Examiner* — Lynnsy Schneider
(74) *Attorney, Agent, or Firm* — Hoffmann & Baron, LLP

(57) ABSTRACT

An implantable spinal disk including an external shell, first endplate, second endplate and core component. The external shell includes sidewalls, a back wall, a front wall, a top surface and a bottom surface forming a compartment. The first endplate includes a first base, first top and first attachment devices. The first base is disposed in the compartment. The first top is disposed in a first opening in the top surface. The first attachment devices extend from within the first top portion. The second endplate includes a second base, second top and second attachment devices. The second base is disposed in the compartment. The second top is disposed in a second opening in the bottom surface. The second attachment devices extend from the second top. The core component is disposed in the compartment between the first endplate and the second endplate.

21 Claims, 7 Drawing Sheets

U.S. PATENT DOCUMENTS

| | | | | |
|---|---|---|---|---|
| 7,645,301 | B2* | 1/2010 | Hudgins et al. | 623/17.12 |
| 2001/0051829 | A1* | 12/2001 | Middleton | 623/17.16 |
| 2002/0035400 | A1* | 3/2002 | Bryan et al. | 623/17.15 |
| 2002/0128715 | A1* | 9/2002 | Bryan et al. | 623/17.15 |
| 2003/0135277 | A1* | 7/2003 | Bryan et al. | 623/17.12 |
| 2003/0220649 | A1* | 11/2003 | Bao et al. | 606/90 |
| 2004/0093087 | A1 | 5/2004 | Ferree et al. | |
| 2004/0098131 | A1* | 5/2004 | Bryan et al. | 623/17.15 |
| 2004/0167626 | A1 | 8/2004 | Geremakis et al. | |
| 2004/0243238 | A1* | 12/2004 | Arnin et al. | 623/17.12 |
| 2005/0015150 | A1 | 1/2005 | Lee | |
| 2005/0027362 | A1* | 2/2005 | Williams et al. | 623/17.11 |
| 2005/0055099 | A1* | 3/2005 | Ku | 623/17.16 |
| 2005/0119752 | A1 | 6/2005 | Williams et al. | |
| 2005/0131544 | A1* | 6/2005 | Kuras et al. | 623/17.13 |
| 2005/0154463 | A1 | 7/2005 | Trieu | |
| 2005/0197702 | A1 | 9/2005 | Coppes et al. | |
| 2006/0064170 | A1 | 3/2006 | Smith et al. | |
| 2006/0129240 | A1* | 6/2006 | Lessar et al. | 623/17.14 |
| 2006/0149273 | A1* | 7/2006 | Ross et al. | 606/86 |
| 2006/0155378 | A1 | 7/2006 | Eckman | |
| 2006/0235524 | A1* | 10/2006 | Petit et al. | 623/17.13 |
| 2006/0235525 | A1* | 10/2006 | Gil et al. | 623/17.13 |
| 2006/0235535 | A1 | 10/2006 | Ferree et al. | |
| 2006/0241766 | A1* | 10/2006 | Felton et al. | 623/17.12 |
| 2006/0253199 | A1 | 11/2006 | Lehuec et al. | |
| 2006/0276900 | A1 | 12/2006 | Carpenter | |
| 2007/0073402 | A1 | 3/2007 | Vresilovic et al. | |
| 2007/0135922 | A1 | 6/2007 | Trieu | |
| 2007/0168042 | A1 | 7/2007 | Hudgins et al. | |
| 2007/0179621 | A1 | 8/2007 | McClellan, III et al. | |
| 2007/0203580 | A1* | 8/2007 | Yeh | 623/17.13 |
| 2008/0077242 | A1* | 3/2008 | Reo et al. | 623/17.15 |

FOREIGN PATENT DOCUMENTS

| | | |
|---|---|---|
| WO | WO-9911203 | 3/1999 |
| WO | WO-0013620 | 3/2000 |
| WO | WO 2004073561 A1 * | 9/2004 |
| WO | WO-2006116852 A1 | 11/2006 |

OTHER PUBLICATIONS

Dynardi, "Dynardi Artificial Disc System", [Online]. [retrieved Aug. 10, 2007]. Retrieved from the Internet: <URL: Http://www.zimmerspine.eu/z/ctl/op/global/action/1/id/9035/template/MP/navid/5889>,1 pgs.

Goins, M L., et al., "Nucleus pulposus replacement: an emerging technology.", *Spine J.* Nov.-Dec. 2005;5(6 Suppl):317S-324S., [Online] [retrieved Aug. 22, 2007]Retrieved from the Internet: <URL: http://www.ncbi.nlm.nih.gov/sites/entrez>, 1 pgs.

Kotani, Y, et al., "Artificial intervertebral disc replacement using bioactive three-dimensional fabric: design, development, and preliminary animal study.", *Spine*. May 1, 2002:27(9):929-35; discussion 935-6., [Online] [retrieved Aug. 22, 2007]Retrieved from the Internet: <URL: http://www.ncbi.nlm.nih.gov/sites/entrez>, 1 pgs.

Langrana, N A., et al., "Materials and design concepts for an intervertebral disc spacer. I. fiber-reinforced composite design.", *J Appl. Biomater*. 1994 Summer;5(2):125-32., [Online][retrieved Aug. 22, 2007]Retrieved from the Internet: <URL: http://www.ncbi.nlm.nih.gov/sites/entrez>, 1 pgs.

Lee, C K., et al., "Development of a Prosthetic Intervertebral Disc.", *Spine*. Jun. 1991:16(6 Suppl):S253-5 [Online][retrieved Aug. 22, 2007] Retrieved from the Internet: <URL: http://www.ncbi.nlm.nih.gov/sites/entrez>, 1 pgs.

Spineuniverse, "Artifical Disc Surgery—Cervical Spine", [Online]. [archived Apr. 6, 2004]. Retrieved from the Internet: <URL: http://web.archive.org/web/20040406014843/http://www.spineuniverse.com/displayarticle.php/article2036.html>,3 pgs.

Vuono-Hawkins, M, et al., "Materials and design concepts for an intervertebral disc spacer. II. Multidurometer composite design.", *J. Appl Biomater*. 1995 Summer:6(2):117-23., [Online][retrieved Aug. 22, 2007]Retrieved from the Internet: <URL: http://www.ncbi.nlm.nih.gov/sites/entrez>, 1 pgs.

Zimmer Corporate, "Zimmer Spine at SAS7 Berlin", [Online]. [retrieved Aug. 10, 2007]. Retrieved fromt he Internet: <URL: Http://www.zimmerspine.eu/z/ctl/op/global/action/1/id/9021/template/cP/navid/4152>,2 pgs.

* cited by examiner

IMPLANTABLE SPINAL DISK

CROSS REFERENCE TO RELATED APPLICATIONS

This application claims priority to U.S. Provisional Application No. 60/859,990, entitled "Soft Disk" and filed on Nov. 20, 2006, the disclosure of which is hereby incorporated in its entirety by reference herein.

TECHNICAL FIELD

Example embodiments relate generally to implantable spinal devices. More particularly, example embodiments are directed to an implantable intervertebral spinal disk to reconstruct a damaged spinal disk of a spinal motion segment of the vertebrae and to restore movement thereto, as well as method for assembly of the implantable intervertebral spinal disk.

BACKGROUND

A normal spinal disk is a cylindrical weight-bearing fibrous structure with a non-compressible viscous center. Due to its ability to deform, the spinal disk not only supports normal functional loads of the human body (e.g., load bearing) but also cushions and evenly distributes the pressures or stresses applied with body movement and positioning (e.g., load sharing). The spinal disk articulates between two bony vertebrae, one vertebra above the disk and one vertebra below the disk, through large surface area interfaces known as endplates. An endplate is a thin (e.g., 1 mm-3 mm) approximately round plate (e.g., 2 cm to 4 cm in diameter) of dense bone and cartilage accounting for a majority of the vertebral weight-bearing capacity.

The spinal disk represents just one of the components defining motion or articulation between vertebrae. The other components are two symmetric facet joints that form a triangular arrangement with the spinal disk being disposed in front. The spinal disk functions as a substantial hydraulic spacer between the vertebrae. Vertical loads with flexion, extension, lateral bending or rotation movements applied to the spine cause the spinal disk to deform and create secondary movement between the vertebrae. Movement across the spinal disk is coupled to the movement of the symmetric facet joints, which function similarly to classical joints with relative translation between two opposing surfaces.

The articulations between the vertebrae, including the foregoing spinal disk and facet joints, frequently deteriorate with age or trauma and become a source of pain. Spinal disk deterioration causes the spinal disk to lose its normal consistency and volume, facilitating the spinal disk to collapse and causing abnormally painful motion within the anterior spinal column. Furthermore, the abnormal motion across the spinal disk increases the stresses on the facet joints and accelerates degeneration of the facet joints.

Historically, surgical treatment of spinal disk disorders required fusion or elimination of movement across an abnormal spinal disk. This has been accomplished by allowing bone to grow between adjacent vertebrae and through the disk space of the abnormal spinal disk. Although fusion generally relieved the source of pain, fusion however did not restore normal movement of the fused spinal motion segment. Invariably, fusion eliminates a range of motion in the fused spinal motion segment, limits overall spinal range of motion and places abnormal pressures or stresses on other non-fused normal spinal motion segments with body movement and positioning. Thus, the abnormal pressures or stresses caused by fusion may further accelerate the degeneration of the foregoing articulations between normal vertebrae.

A new class of restorative or motion preserving spinal devices has been introduced to overcome the foregoing limitations of fusion. These motion preserving spinal devices aim to restore and maintain spinal disk height while approximating a range of motion and function of the normal spinal disk.

The motion preserving spinal devices include artificial spinal disks that generally have rigid movably coupled components and ball-socket articulation. More specifically, the artificial spinal disks function through direct contact and movement between two opposing surfaces, usually metal or plastic. The ball-socket articulation (among other mechanical contact points) produce hazardous debris and cannot reproduce adequately normal spinal disk deformation or its load sharing capacity. The mechanical contact points (including ball-socket articulation) of the artificial spinal disk components wear with repetitive motion and produce debris which may induce scarring, toxicity and bone absorption. The scarring may be extensive with the potential for neural injury and bone loss. Certain debris (e.g., nickel) accumulates in the body and may cause systemic toxicity. The mechanical wear further may cause breakdown of artificial spinal disk components and resultant painful malfunction of the artificial spinal disk. Furthermore, non-constrained components may extrude into the abdomen with disastrous consequences.

One way of approximating the motion of the normal spinal disk has been to implement a floating center of movement. However, computer simulations using finite element analysis of currently available artificial spinal disks have shown excessive or abnormal motion at spinal disk interfaces, particularly in extension, when compared to the normal spinal disk. These data have been confirmed by biomechanical testing of the artificial spinal disks in cadavers. The abnormal motion at the artificial disk interfaces wears artificial spinal disk components and puts abnormal strain on the facet joints of the vertebrae, significantly accelerating painful and debilitating degeneration of the vertebrae.

While the new class of restorative or motion preserving spinal devices aims to solve the limitations of fusion, the foregoing abnormal strain on the facet joints, the wear of the artificial spinal disk with resultant debris and possible failure of the artificial spinal disk increase painful and debilitating degeneration of the vertebrae and may further in the case of extrusion present real dangers to one's health.

BRIEF DESCRIPTION OF THE DRAWINGS

Some embodiments are illustrated by way of example and not limitation in the figures of the accompanying drawings in which.

DETAILED DESCRIPTION

An example implantable intervertebral spinal disk and method for assembling the implantable intervertebral spinal disk are described. In the following description, for the purposes of explanation, numerous specific details are set forth in order to provide a thorough understanding of example embodiments. It will be evident, however, to one skilled in the art that an example embodiment may be practiced without these specific details.

Figure 1:
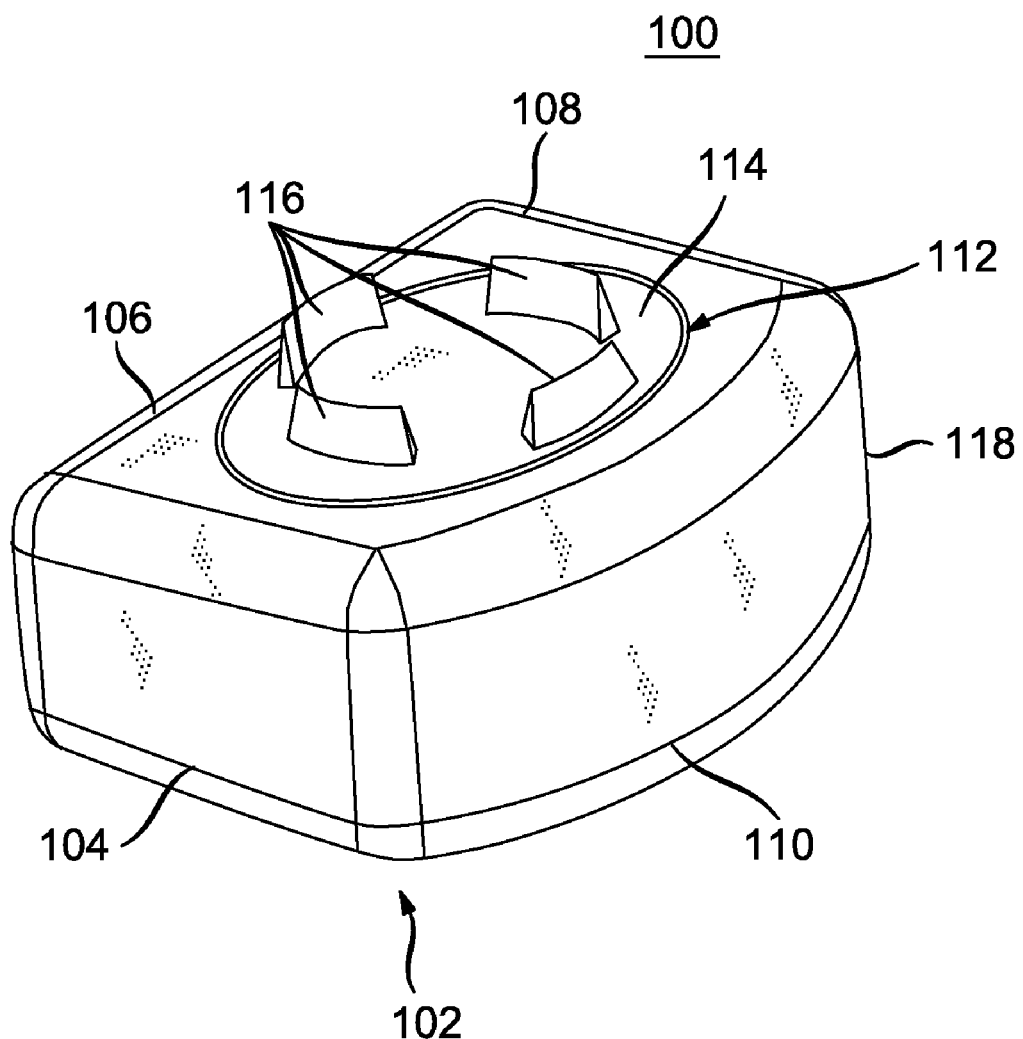
FIG. 1 is a perspective view of an implantable intervertebral spinal disk.

FIG. 1 is a perspective view 100 of an example implantable intervertebral spinal disk 102 adapted to restore spinal disk height and to approximate closely the biomechanics of a normal spinal disk, mitigating abnormal strain on the facet joints, debris and possible failure caused by the conventional implantable spinal devices. The implantable intervertebral spinal disk 102 is suitable for the arthroplasty of the cervical, the thoracic and the lumbar spine. The implantable intervertebral spinal disk 102 comprises an external shell 118 illustrated in detail in FIG. 4 and described hereinbelow with reference to the same, and plural internal components illustrated in detail in FIGS. 2-7 and described hereinbelow with reference to the same. The internal components include a pair of endplates (illustrated in detail in FIGS. 5 and 6 and described hereinbelow) and a core internal component (illustrated in detail in FIG. 7 and described hereinbelow) sandwiched between the pair of endplates. The external shell 118 is viscoelastic, a flexible non-compressible solid that is deformable and yet sufficiently resilient to stress or pressure of body movement and positioning. The external shell 118 includes plural openings, one on a top surface thereof and one on a bottom surface thereof (e.g., opening 112), through which the respective endplates protrude. The plural openings are generally oval for ease of manufacturing, assembly and the like. However, the shapes of the openings are not limited and a variety of other shapes may easily be implemented. The openings expose respective contact surfaces (e.g., contact surface 114 exposed through opening 112) for the integration between the endplates and the bony vertebrae. The bone of each vertebra (e.g., above and below the implantable intervertebral spinal disk 102) will grow and bind to the respective contact surface (e.g., contact surface 114) of each endplate but not to the external shell 118 as will be described below. The openings should be as large as possible to provide the largest endplate-bone contact surfaces, yet also function to retain the endplates within the exterior shell 118 as will also be described below. To improve the retention of the endplates within the exterior shell 118, a groove may be provided on the upper covered surfaces of the endplates with corresponding ridges on the interior of each exterior shell 118. This provides a securing mechanism to mitigate the possibility of the external shell 118 rolling off the endplates with the operation of the implantable intervertebral spinal disk 102.

Further with reference to FIG. 1, the external shell 118 includes side surfaces 104, 108, a back surface 106 and a front surface 110. The side surfaces 104, 108 and the back surface 106 are generally flat surfaces, while the front surface 110 is a generally curve-shaped or arcuate surface. Additionally, the side surfaces 104, 108 gradually increase in height from the back surface 106 to the front surface 110. More specifically, the implantable intervertebral spinal disk 102 is taller in front than in the back to provide for the natural curvature of the cervical or lumbar segments of the spine into which the implantable intervertebral spinal disk 102 will most often be implanted. The degree of the implantable intervertebral spinal disk 102 triangulation varies between different levels of the spine (e.g., cervical, lumbar, thoracic) and between different people. The endplates will generally provide between a zero (0) and a six (6) degree angle with a horizontal plane through the center of the implantable intervertebral spinal disk 102 (e.g., through the center of the core internal component). The combined angle of the plural endplates will most commonly be between three (3) and six (6) degrees. The height of the implantable intervertebral spinal disk 102 may vary about 12 mm to about 20 mm in the front, and from about 2 mm to about 3 mm shorter in the back (e.g., about 9 mm to about 17 mm). The implantable intervertebral spinal disk 102 is about 30 mm to about 35 mm wide (between side surfaces 104, 108), about 20 mm to about 25 mm deep (between back surface 106 and front surface 110), and about 10 mm to about 15 mm high (from contact surface to contact surface). The attachment devices 116 on each contact surface are about 4 mm high. The foregoing overall dimensions of the implantable intervertebral spinal disk 102 (as well as the dimensions of internal components that are described below) may be varied for the different levels of the spine (e.g., cervical, lumbar, thoracic) and for different people.

Still further with reference to FIG. 1, each of the endplates includes a base portion that is wider than the respective opening to be contained by the external shell 118, an upper portion that approximates the size, shape and height of the opening and that fits in the opening, and plural attachment devices 116 that protrude through the opening. The base portion of the endplates is bounded by the external shell. The upper portion of the endplates forms a continuous surface (e.g., contact surface 114) with the exterior shell 118. The contact surface (e.g., contact surface 114) may be planar or convex (e.g., contact surface 114 rounded outward) to fit the geometry of the vertebrae. However, the contact surface is not limited and may be variable or even custom shaped to fit a particular disk space between the vertebrae. The plural attachment devices 116 of each endplate are projections in a geometric arrangement adapted to penetrate into a respective vertebra and anchor the vertebra, inducing bony ingrowths to integrat or fixate the example implantable intervertebral spinal disk 102 between vertebrae. Each of the plural attachment devices 116 is generally of a trapezoidal shape with a triangular cross-section (wedge shape) in the vertical dimension to achieve easier penetration into the vertebrae and is curve-shaped or arcuate in the horizontal dimension. The plural attachment devices 116 may be disposed in a generally oval or circular arrangement on the upper portion 114 of the endplates. The shape of the plural attachment devices 116 and the arrangement of the plural attachment devices 116 on the contact surfaces are adapted to further mitigate translation (side-to-side) movement and rotational movement.

Yet further with reference to FIG. 1, other arrangements of the plural attachment devices 116 are of course possible. Each of the plural attachment devices 116 may be similarly or differently shaped. Furthermore, the plural attachment devices 116 may include spikes, keels, flanges and the like to fixate the intervertebral spinal disk 102 to the vertebrae. Still further, the plural attachment devices 116 may be irregularities on the contact surfaces to increase friction, small teeth, or ridges running in the same or different directions. The shape of ridges can be symmetrically triangular and may point back like shark teeth. Yet further, a single ridge or several ridges may be disposed on the contact surfaces from front to back of the implantable intervertebral spinal disk 102 that may be impacted into the vertebra. The plural attachment devices 116 may include a tag like extension wrapping in front of the vertebra with holes for screws that fixate the implantable intervertebral spinal disk 102 to the vertebrae. Still further, spikes, hooks or other fixation devices may be concealed within a center of the endplates and engaged when the implantable intervertebral spinal disk 102 is inserted into the disk space between the vertebrae.

Figure 2:
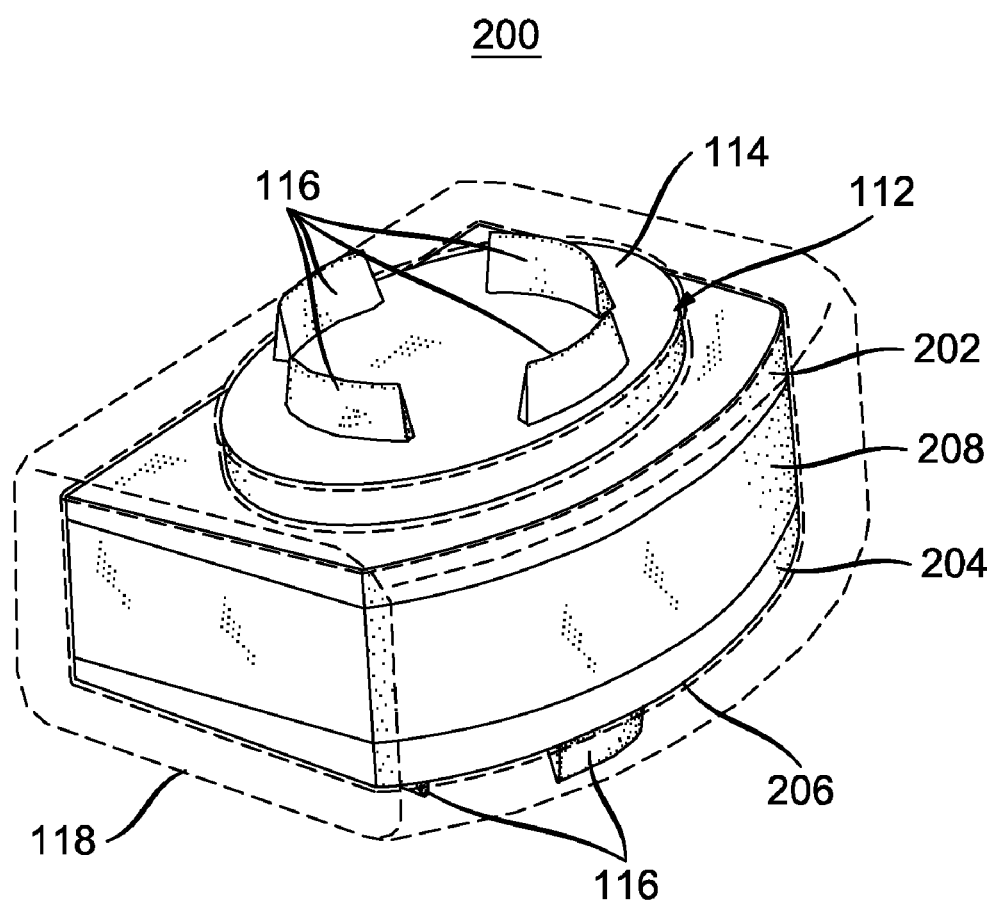
FIG. 2 is a semi-transparent perspective view of the implantable intervertebral spinal disk in accordance with FIG. 1.

FIG. 2 is a semi-transparent perspective view 200 of the implantable intervertebral spinal disk 102 in accordance with FIG. 1. The external shell 118 is shown to be transparent to illustrate internal components of the implantable intervertebral spinal disk 102. As described in reference to FIG. 1 above and shown in greater detail in FIG. 2, the internal components include a pair of opposing endplates 202, 204, and a core internal component 208 sandwiched between the pair of endplates 202, 204. Endplate 202 includes a contact surface 114 with attachment devices 116 arranged thereon in a first arrangement and opposing endplate 204 includes a contact surface 206 with attachment devices 116 arranged thereon in a second arrangement. The attachment devices 116 of the first and second arrangements may be similarly or differently shaped, and further may be arranged similarly or differently on the respective contact surfaces 114, 206.

Further with reference to FIG. 2, the core internal component 208 will be described in greater detail with reference to FIG. 7 herein below. At this point it is sufficient to note that the core internal component 208 is viscoelastic, a flexible non-compressible solid or liquid that is deformable and yet sufficiently resilient to stress or pressure of body movement and positioning. It is also noted here that here and will be described in greater detail hereinafter that the external shell 118 is generally stiffer then the core internal component 208. The external shell 118 is adapted not only to contain or bound the internal components 202, 204 and 208, but also to provide sufficient inward vertical pressure during operation between the internal components, 202, 204, and 208 and inward lateral pressure on the internal components 202, 204 and 208. During operation the pressures on the implantable intervertebral spinal disk 102 may be substantial and may change or shift about the implantable intervertebral spinal disk 102 with different body movements (e.g., sitting, standing, bending, and/or twisting movements). Under these pressures the implantable intervertebral spinal disk 102 deforms vertically (generally with insignificantly) with range of angulation of about 4 degrees to about 5 degrees in flexion and about 2 degrees to about 3 degrees in extension. The external shell 118 is resilient to mitigate movement or shifting (side to side and/or back to front) between the internal components 202, 204 and 208.

In addition, the core internal component 208 is preloaded in the external shell 119 to produce outward pressure, expanding or stretching the external shell 118 about internal components 202, 204 and 208, and further pressing the endplates 202, 204 respectively up and down against the external shell 118 and the adjacent vertebrae. Thus, the external shell 118 and the core component 208 provide for sufficient pressure between internal components 202, 204 and 208 to mitigate the movement or shifting between the internal components 202, 204, and 208 under varying stresses applied to the spine (e.g., flexion, extension, lateral bending or rotation movements) causing the core internal component 208 to deform during the operation of the intervertebral spinal disk 102. In addition to the foregoing inward and outward pressures, because the endplates 202, 204 protrude through the external shell 118 and have a tight fit therethrough (e.g., through opening 112), movement or shifting of the these internal components 202, 204 is further restrained during the operation of the intervertebral spinal disk 102.

Figure 3:
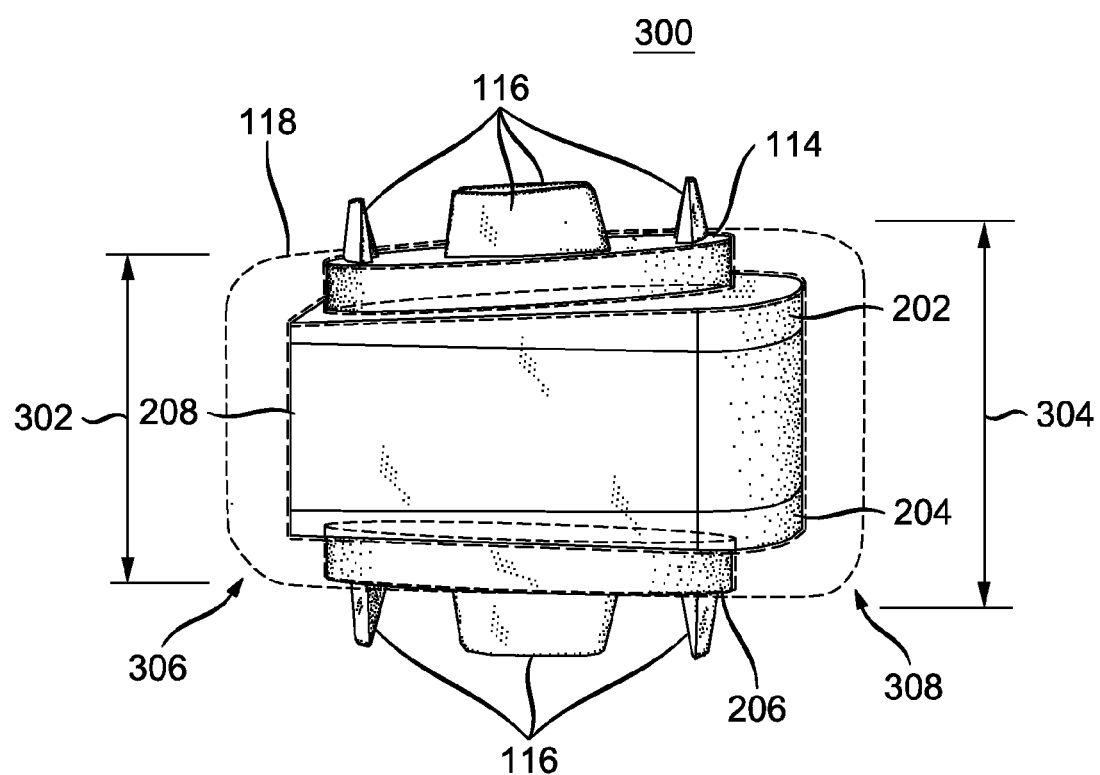
FIG. 3 is a semi-transparent side view of the implantable intervertebral spinal disk in accordance with FIG. 1.

FIG. 3 is a semi-transparent side view 300 of the implantable intervertebral spinal disk 102 in accordance with FIG. 1. As illustrated in the side view 300, the height 302 at the rear 306 of the implantable intervertebral spinal disk 102 is greater than the height 304 at the front 308 of the implantable intervertebral spinal disk 102. The rise between the rear 306 and the front of the implantable intervertebral spinal disk 102 is adapted to approximate the disk space between vertebrae into which the implantable intervertebral spinal disk 102 is to be implanted, aligning the vertebrae in their natural position in relation to each other. As noted hereinbefore, contact surfaces 114, 206 may be of approximately parallel configuration for thoracic uses, may have varying rise configurations for lumbar and cervical uses, and/or may accommodate individual anatomy for any of the foregoing segments of the spine (e.g., thoracic, lumbar, cervical) into which the implantable intervertebral spinal disk 102 is to be implanted. The height 304 of the implantable intervertebral spinal disk 102 may vary from about 12 mm to about 20 mm at the front 308, and from about 2 mm to about 3 mm shorter at the back 306 (e.g., about 9 mm to about 17 mm). As described with reference to FIG. 1 above, the implantable intervertebral spinal disk 102 is about 30 mm to about 35 mm wide, about 20 mm to about 25 mm deep, and about 10 mm to about 15 mm high (from contact surface 114 to contact surface 206). The attachment devices 116 on each contact surface 114, 206 are about 4 mm high. The overall size of the implantable intervertebral spinal disk 102, as well as the differences in heights 302, 304 to achieve a different rise, may be configured or adjusted based on a particular patient's vertebral dimensions (anatomy) and configuration of the vertebral space between vertebrae into which the implantable intervertebral spinal disk 102 is to be implanted. As illustrated in the side view 300, the height of the core internal component 208 is approximately the same throughout the component.

Further with reference to FIG. 3, the height of the endplates 202, 204 may be varied from the rear 306 to the front 308 to achieve the desired heights 302, 304 at the respective rear 302 and front 304 of the implantable intervertebral spinal disk 102. More specifically, the height of base portion of the endplates 202, 204 (described in greater detail in reference to FIGS. 5 and 6 hereinbelow) may be varied similarly for each endplate 202, 204 from the rear 306 to the front 308 to achieve the desired heights 302, 304 of the implantable intervertebral spinal disk 102. It is noted, however, that the heights of the front and rear of each of the endplates 202, 204 may be adjusted independently to maintain the same overall shape of the implantable intervertebral spinal disk 102, yet achieve a relatively different angle of the core internal component 208 relative to the configuration of the vertebral space between vertebrae into which the implantable intervertebral spinal disk 102 is to be implanted. It is further noted that the overall heights 302, 304 may also be achieved by varying the height between the rear and the front of the core internal component 208, or by the combination of the core internal component 208 and the endplate 202, 204.

Figure 4:
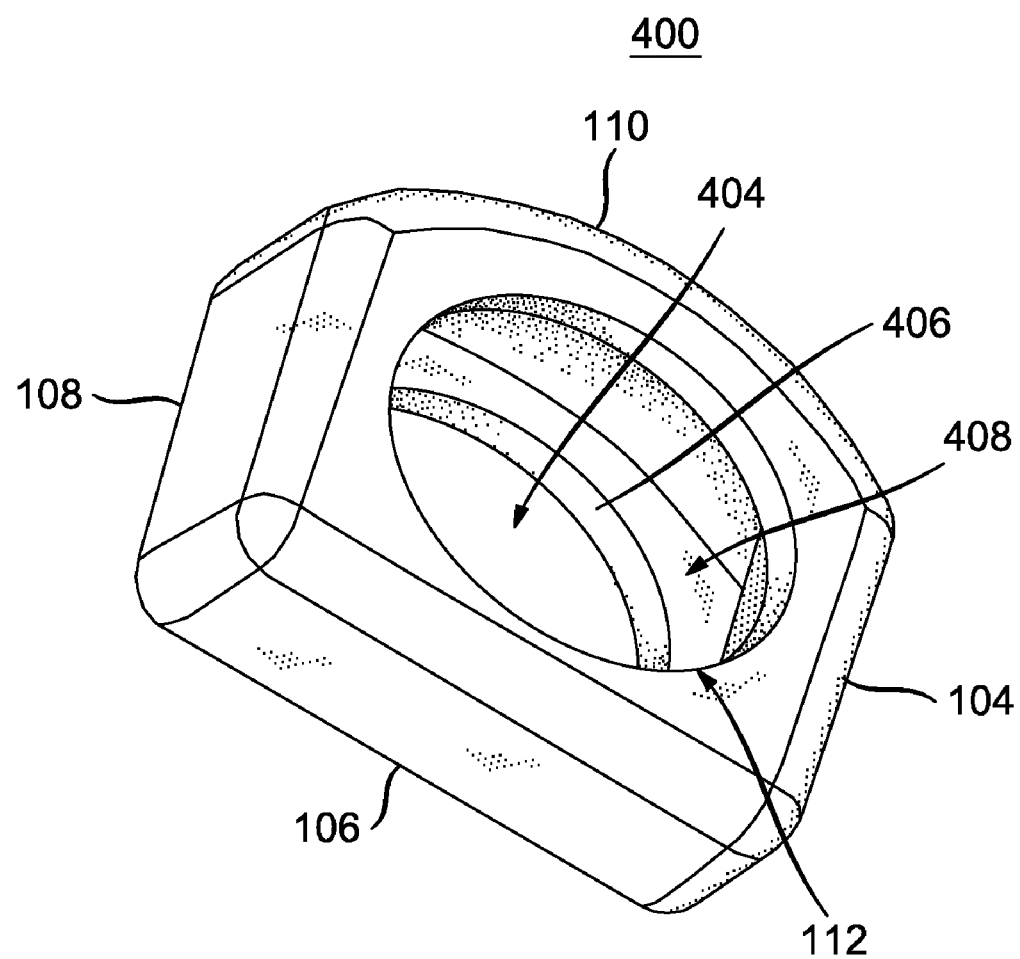
FIG. 4 is a perspective view of an outer shell of the implantable intervertebral spinal disk in accordance with FIG. 1.

FIG. 4 is a perspective view 400 of an exterior shell 118 of the implantable intervertebral spinal disk 102 in accordance with FIG. 1. The exterior shell 118 is adapted to contain the internal components 202, 204 and 208 as described hereinabove, while providing inward pressure on the internal components when loaded into the exterior shell 118. The external shell 118 is made of a biocompatible and bio-stable (non-biodegradable) material that is viscoelastic, a flexible non-compressible solid that is deformable and yet sufficiently resilient to stress or pressure of body movement and positioning. The exterior shell 118 should have a Youngs modulus of elasticity of about 7 MPa to about 13 MPa. A variety of elastomers, such as polyurethanes, silicones, hydrogels, collagens, hyalurons, proteins and other synthetic polymers can be used to achieve the foregoing biocompatibility, bio-stability and the range of viscoelastic properties.

Further with reference to FIG. 4, the exterior shell 118 includes a first oval opening 112 and a second oval opening 404 to secure respective endplates 202, 204, yet facilitate the protrusion of plural attachment devices 116 through openings 112, 404. As already mentioned hereinabove in reference to FIG. 1, the openings may be of a different shape. The dimensions of the openings 112, 404 may be from about 15 mm to about 25 mm. The exterior shell 118 has a thickness 406 from about 1 mm to about 2 mm to provide deformation and elasticity (e.g., about 7 MPa to about 13 MPa) and an interior space (or compartment) 408 to contain internal components 202, 204 and 208 as described herein.

Figure 5:
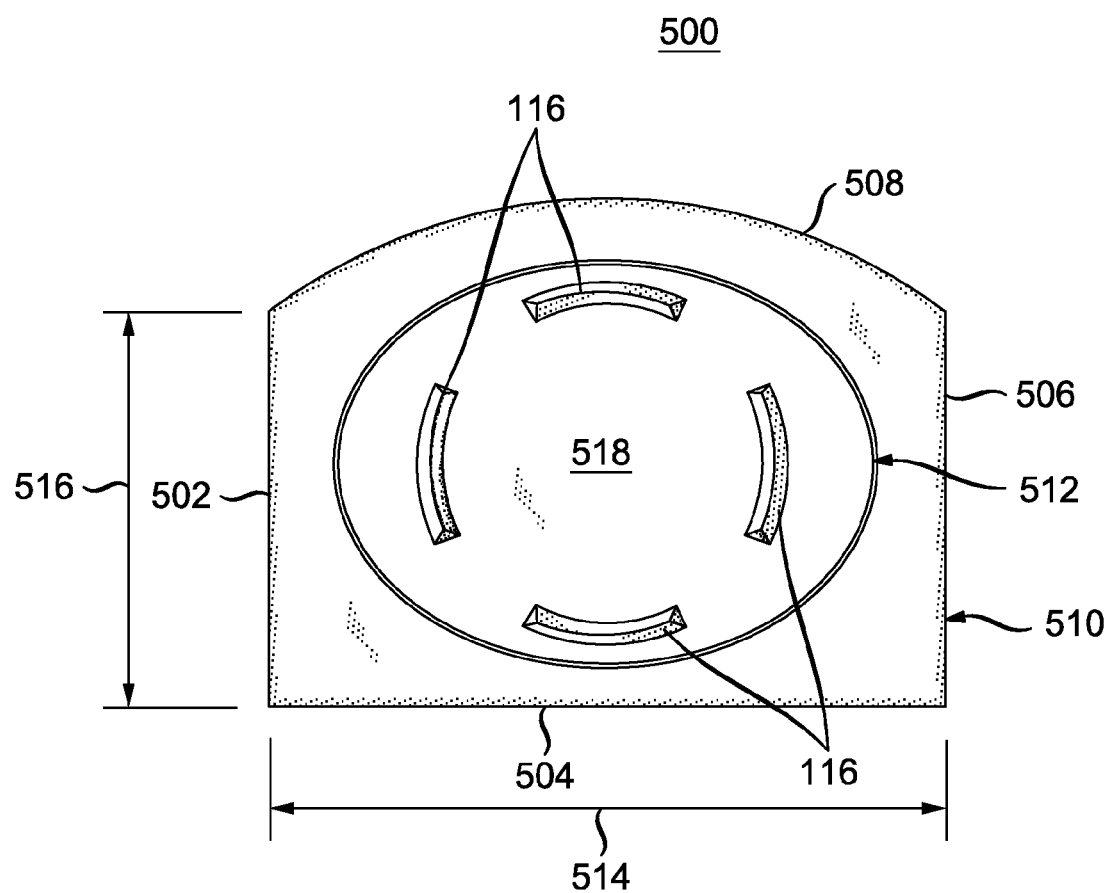
FIG. 5 is a top view of the an endplate of the implantable intervertebral spinal disk in accordance with FIG. 1.

FIG. 5 is a top view 500 of an endplate 202, 204 of the implantable intervertebral spinal disk 102 in accordance with FIG. 1 The endplates 202, 204 are made of a biocompatible metal, such as titanium, stainless steel or other biocompatible metal. The endplate 202, 204 has a base portion 510 that is defined by approximately straight sides 502, 506 (e.g., from about 17 mm to about 22 mm), straight back 504 (e.g., about 25 mm to about 30 mm wide) that is approximately perpendicular to the sides 502, 506, and a curve-shaped or arcuate front 508. Atop the base portion and approximately centrally disposed thereon is a top portion 512 that is oval-shaped to fit the openings of the exterior shell 118 (e.g., openings 112, 404). The top portion 512 may be shaped differently (e.g., other than oval) to fit differently-shaped exterior shell 118 openings. What is important to note is that the top portion 512 should be as large as possible to provide the largest endplate-bone contact surface 518 (e.g., contact surfaces 114, 206 of FIGS. 1-3) for integration between the endplate 202, 204 and the bony vertebrae, yet provide a sufficient base portion 510 to be retained securely within the exterior shell 118. Furthermore, atop the top portion 512 on the contact surface 518 there are disposed attachment devices 116 in approximately oval or circular arrangement. As described hereinabove with reference to FIG. 1, the attachment devices 116 are adapted to penetrate into respective vertebra and induce bony ingrowths.

Further with reference to FIG. 5, the contact surface 518 may further be coated with calcium phosphate, hydroxyapatite, ceramics, biomimetic apatites, bioactive glass, covalently attached bioactive conjugates such as osteopontin, bone sialoprotein, bone acidic glycoprotein-75, osteocalcin, bone morphogenic proteins, transforming growth factors, laminin, type IV collagen, type VIII collagen, enamel proteins, cell adhesion peptides, prostaglandins, serum proteins, glucocorticosteroids, phosphoserine, pyrophosphates, phosphothreonine, phosvitin, phosphophoryn, phosphonates, phosphotases and bone and epithelial proteoglycans, as well as other osteoinductive and osteoconductive materials.

Figure 6:
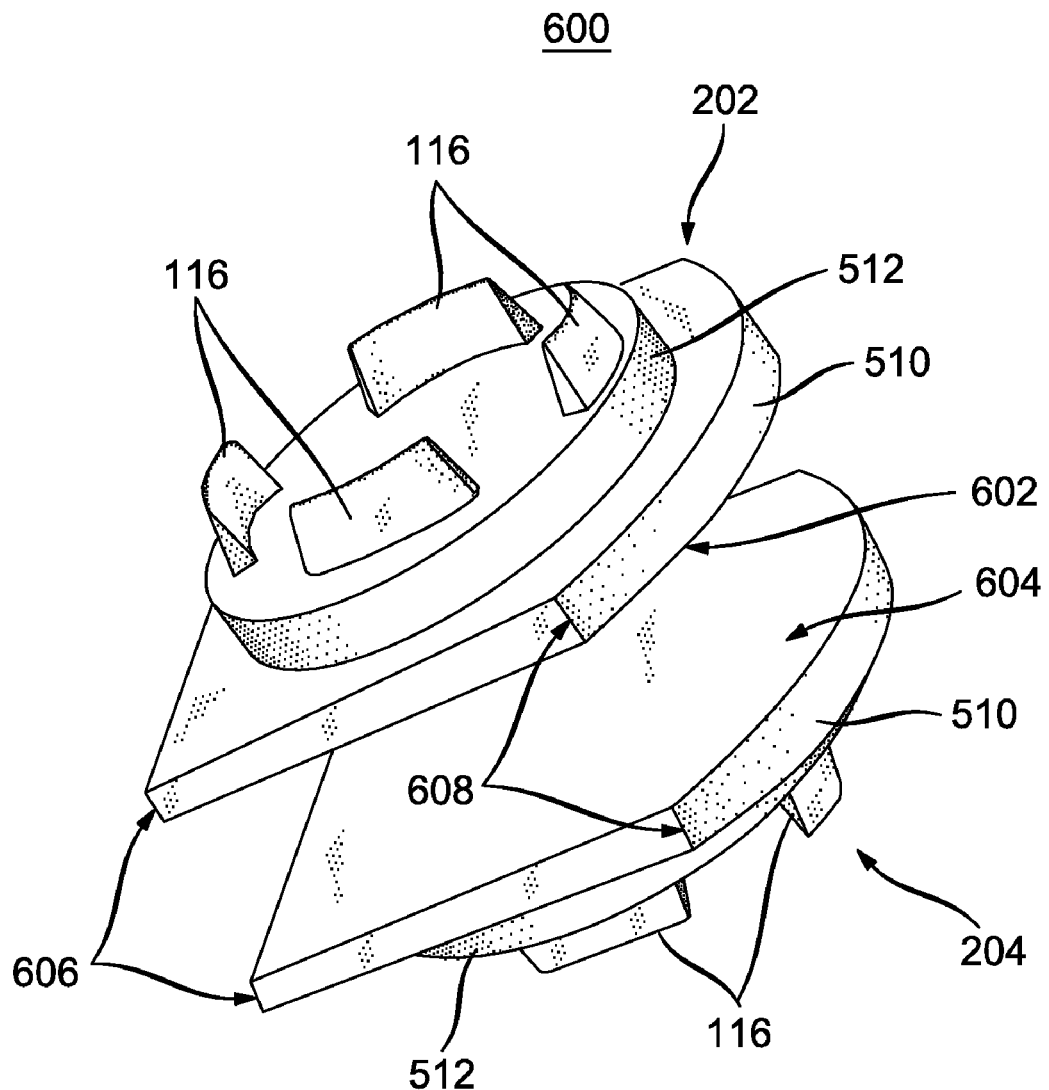
FIG. 6 is a perspective view of a pair of endplates of the implantable intervertebral spinal disk in accordance with FIGS. 1 and 5.

FIG. 6 is a perspective view 600 of a pair of endplates 202, 204 of the implantable intervertebral spinal disk 102 in accordance with FIGS. 1 and 5. The endplates 202, 204 include respective base portions 510, top portions 512 and attachment devices 116. The base portions 510 of endplates 202, 204 have respective planar surfaces 602, 604 for mating with a planar surface of the core internal component 208 shown in greater detail in FIG. 6. The base portions 510 of endplates 202, 204 further have varying heights 606 and 608 described hereinabove in greater detail in reference to FIG. 3. Although the heights 606, 608 may be varied to achieve various angulation as described herein in relation to FIG. 3, the height 606 may be about 1 mm to 1.5 mm, while height 608 may be about 2 mm to about 2.5 mm.

Figure 7:
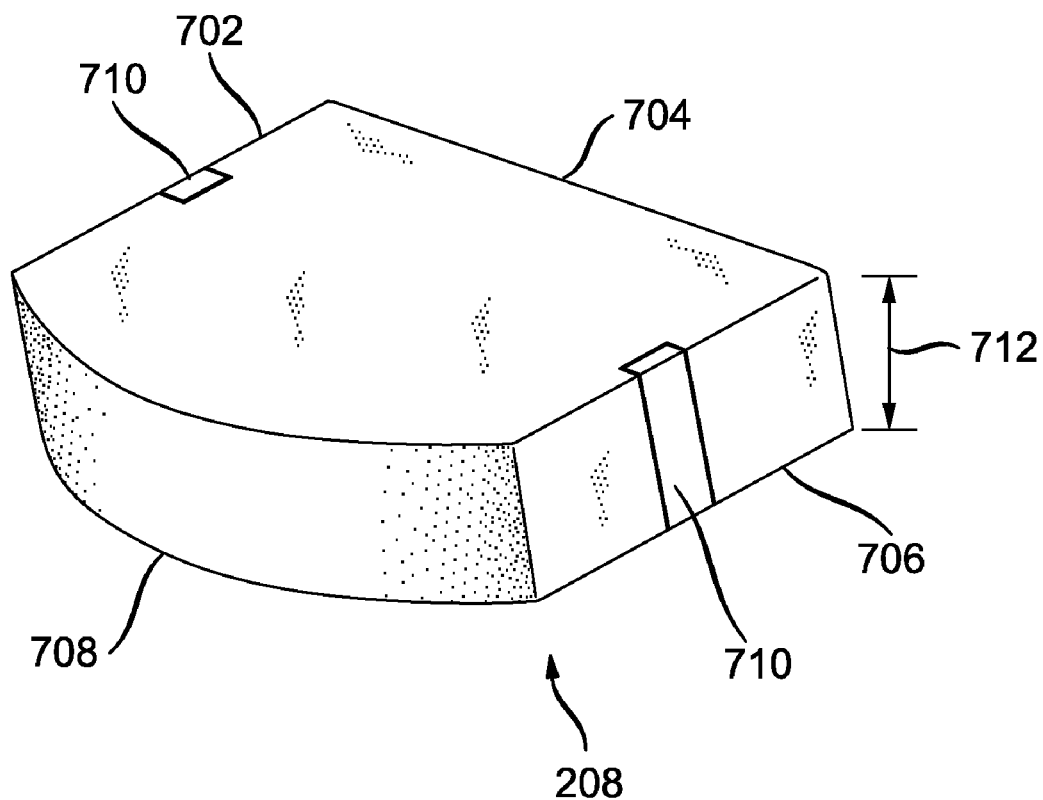
FIG. 7 is a perspective view of a core internal component of the intervertebral spinal disk in accordance with FIG. 1.

FIG. 7 is a perspective view 700 of a core internal component 208 of the intervertebral spinal disk 102 in accordance with FIG. 1. The core internal component 208 has similar dimensions to the base portions 510 of endplates 202, 204. More specifically, the core internal component 208 is defined by approximately straight sides 702, 706 (e.g., from about 17 mm to about 22 mm), straight back 704 (e.g., about 25 mm to about 30 mm wide) that is approximately perpendicular to the sides 702, 706, and a curve-shaped or arcuate front 708. The core internal component 208 has a height 712 of about 6 mm to about 8 mm.

Further with reference to FIG. 7, the core internal component 208 is made of a biocompatible and bio-stable (non-biodegradable) material that is viscoelastic, a flexible non-compressible solid that is deformable and yet sufficiently resilient to stress or pressure of body movement and positioning. The core internal component 208 should have a Youngs modulus of elasticity of about 3 MPa to about 8 MPa. A variety of elastomers, such as polyurethanes (e.g., polycarbonated urethane), silicones, hydrogels, collagens, hyalurons, proteins and other synthetic polymers (e.g., injectable polymers) can be used to achieve the foregoing biocompatibility, bio-stability and the range of viscoelastic properties. The core internal component 208 may be pre-fabricated into a solid and assembled into the implantable intervertebral spinal disk 102 before implantation or may be injected into a constrained space between the endplates 202, 204, such as via a balloon between the endplates 202, 204, after the implantable intervertebral spinal disk 102 is implanted between the vertebrae. The core internal component 208 may, but need not, include vertical reinforcement columns 710 made of a stiffer viscoelastic material. For example, if the implantable intervertebral spinal disk 102 is narrow (which may present a placement advantage because side to side exposure requires getting around big blood vessels), a pair of vertical reinforcement columns 710 may be inserted into sides 702, 706 of the core internal component 208 through similarly shaped vertical cut-outs in the core internal component 208. The vertical reinforcement columns 710 may have a Youngs modulus of elasticity between 6 MPa to about 13 MPa (e.g., greater than the Youngs modulus of elasticity of the core internal component itself).

In accordance with FIGS. 1-7, the implantable intervertebral spinal disk 102 may be made of pre-fabricated exterior shell 118 and internal components 202, 204 and 208, assembled into implantable intervertebral spinal disk 102, which is then inserted into the disk space between vertebrae. In the assembly process, one of the endplates 202, 204 is inserted into interior space 408 of exterior shell 118 through one of the openings 112, 404 by stretching the viscoelastic exterior shell 118 around the base portion 510 of the endplate 202, 204. A metal bar or like assist instrument (e.g., screwdriver) may be used to assist in stretching the exterior shell over the endplate 202, 204. A portion of the endplate 202, 204 is placed in the opening 112, 404. The assist instrument may then be placed over that portion of the endplate 202, 204 and under the exterior shell 208 through the opening 112, 404. The assist instrument is then mechanically traced about the opening 112, 404 until the exterior shell covers the base portion 510 of endplate 202, 204 and the top portion 512 is in the opening 112, 404. Once the first endplate 202, 204 is inserted into the interior space 408 of the exterior shell 118, the core internal component 208 may be inserted into the interior space 408 of the exterior shell 118 through the opposite opening 112, 404 in a similar fashion. The other of the endplates 202, 204 is then inserted into interior space 408 of exterior shell 118 through the same opening 112, 404 as the core internal component 208 in a similar fashion. The assembled implantable intervertebral spinal disk 102 is thereafter inserted in the disk space between the vertebrae.

Further in accordance with FIGS. 1-7, the implantable intervertebral spinal disk 102 may also partially pre-fabricated and assembled into implantable intervertebral spinal disk 102, which is then inserted into the disk space between vertebrae and completed after insertion. More specifically, one of the endplates 202, 204 is inserted into interior space 408 of exterior shell 118 through one of the openings 112, 404. An empty balloon that will form the core internal component 208 once completed may be inserted into the interior space 408 of the exterior shell 118 through the opposite opening 112, 404. The other of the endplates 202, 204 is then inserted into interior space 408 of exterior shell 118 through the same opening 112, 404 as the balloon that will form the core internal component 208. The implantable intervertebral spinal disk 102 is then inserted into the disk space between vertebrae. The balloon is thereafter filled with a viscoelastic injectable polymer to complete the fabrication and implantation of the implantable intervertebral spinal disk 102.

In operation in accordance with reference to FIGS. 1-7, the implantable intervertebral spinal disk 102 restores spinal disk height and approximates closely the biomechanics of a normal spinal disk, mitigating abnormal strain on the facet joints and debris caused by the conventional implantable spinal devices, as well as the likelihood of failure or extrusion of the components of the implantable intervertebral spinal disk 102.

Thus, an example implantable intervertebral spinal disk and method for assembling the implantable intervertebral spinal disk have been described. Although specific example embodiments have been described, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

What is claimed is:

1. An implantable spinal disk comprising:
an external shell including a pair of sidewalls, a back wall, a front wall, a top surface and a bottom surface forming a compartment therebetween, the top surface including a first opening of a first dimension and the bottom surface including a second opening of a second dimension;
a first endplate including a first base portion, a first top portion and a plurality of first attachment devices, the first base portion of a dimension greater than the first dimension of the first opening and disposed in the compartment, the first top portion of a dimension smaller than the dimension of the first base portion and approximately the dimension of the first dimension of the first opening and disposed in the first opening, the first top portion having a uniform first perimeter along vertical axis, and the plurality of first attachment devices extending from within the first perimeter of the first top portion and being configured to penetrate into a first vertebra, an upper surface of the first top portion forming a first contact surface continuous with the top surface of the external shell, the first contact surface configured to integrate with the first vertebra;
a second endplate including a second base portion, a second top portion and a plurality of second attachment devices, the second base portion of a dimension greater than the second dimension of the second opening and disposed in the compartment, the second top portion of a dimension smaller than the dimension of the second base portion and approximately the dimension of the second dimension of the second opening and disposed in the second opening, the second top portion having a uniform second perimeter along vertical axis, and the plurality of second attachment devices extending from within the second perimeter of the second top portion and being configured to penetrate into a second vertebra, an upper surface of the second top portion forming a second contact surface continuous with the bottom surface of the external shell, the second contact surface configured to integrate with the second vertebra; and
a core internal component disposed in the compartment between the first endplate and the second endplate, wherein the external shell is stiffer than the core internal component.

2. The implantable spinal disk of claim 1, wherein the external shell is made of a viscoelastic material having a Youngs modulus of elasticity of between about 7 MPa and about 13 MPa.

3. The implantable spinal disk of claim 1, wherein the core internal component is made of a viscoelastic material having a Youngs modulus of elasticity of between about 3 MPa and about 8 MPa.

4. The implantable spinal disk of claim 1, wherein the core internal component includes at least one vertical reinforcement column made of a viscoelastic material having a Youngs modulus of elasticity of between about 6 MPa and about 13 MPa.

5. The implantable spinal disk of claim 1, wherein the core internal component is a balloon filled with an injectable viscoelastic material having a Youngs modulus of elasticity of between about 3 MPa and about 8 MPa.

6. The implantable spinal disk of claim 1, wherein the core internal component produces outward vertical pressure on the first endplate and the second endplate against the external shell.

7. The implantable spinal disk of claim 1, wherein the external shell produces inward vertical and lateral pressure on the first endplate, the second endplate, and the core internal component to mitigate movement of the first endplate, the second endplate and the core internal component in relation to each other with a load applied through the first vertebra and the second vertebra that deforms the core internal component.

8. The implantable spinal disk of claim 1, wherein the first endplate and the second endplate are made of metal.

9. The implantable spinal disk of claim 1, wherein at least one of the first base portion and the second base portion is angled at an angle with respect to a horizontal plane through a center of the core internal component.

10. The implantable spinal disk of claim 9, wherein the angle is between zero and six degrees.

11. The implantable spinal disk of claim 1, wherein the pair of sidewalls is approximately perpendicular to the back wall and the front wall forms an arcuate shape between the sidewalls.

12. The implantable spinal disk of claim 1, wherein at least one of the first opening and the second opening is of an oval or circular shape.

13. The implantable spinal disk of claim 1, wherein the plurality of first attachment devices and the plurality of second attachment devices are disposed in a respective first geometric arrangement and a second geometric arrangement on the respective first contact surface and second contact surface.

14. The implantable spinal disk of claim 1, wherein at least one of the plurality of first attachment devices or at least one of the plurality of second attachment devices is a spike, hook, keel, flange, tag, surface irregularity, tooth, or ridge.

15. The implantable spinal disk of claim 14, wherein the ridge is at an angle with respect to the first top portion or the second top portion.

16. The implantable spinal disk of claim 14, wherein the spike or hook is configured to be retained within the first endplate or the second endplate and further configured to extend though the first top portion or the second top portion to engage the respective first vertebra or the second vertebra.

17. The implantable spinal disk of claim 14, wherein the tag includes a hole and is configured to be secured to the first vertebra or the second vertebra with a screw through the hole.

18. The implantable spinal disk of claim 1, wherein at least one of the first contact surface and the second contact surface is one of planar, convex and variable-shape to integrate into the respective first vertebra and second vertebra.

19. The implantable spinal disk of claim 1, wherein the core internal component is injected into the compartment between the first endplate and the second endplate.

20. The implantable spinal disk of claim 1, further comprising a balloon disposed in the compartment between the first endplate and the second endplate, wherein the core internal component is disposed in the balloon.

21. The implantable spinal disk of claim 20, wherein the core internal component is injected into the balloon disposed in the compartment between the first endplate and the second endplate.

\* \* \* \* \*

UNITED STATES PATENT AND TRADEMARK OFFICE
CERTIFICATE OF CORRECTION

| | | |
|---|---|---|
| PATENT NO. | : 8,029,569 B2 | Page 1 of 1 |
| APPLICATION NO. | : 11/939991 | |
| DATED | : October 4, 2011 | |
| INVENTOR(S) | : Joseph Aferzon and Jeffrey A. Bash | |

It is certified that error appears in the above-identified patent and that said Letters Patent is hereby corrected as shown below:

Column 5, line 29:

Now reads: "here that here and"
Should read: --here and--

Column 5, line 43:

Now reads: "generally with insignificantly"
Should read: --generally insignificantly--

Column 7, line 21:

Now reads: "with FIG 1 The"
Should read: --with FIG 1. The--

Signed and Sealed this
Twentieth Day of November, 2012

David J. Kappos
*Director of the United States Patent and Trademark Office*